(12) United States Patent
Mosayyebi et al.

(10) Patent No.: US 11,344,438 B2
(45) Date of Patent: May 31, 2022

(54) STENT WITH STREAMLINED SIDE HOLES

(71) Applicant: University of Southampton, Southampton (GB)

(72) Inventors: Ali Mosayyebi, Southampton (GB); Dario Carugo, Southampton (GB); Costantino Manes, Southampton (GB)

(73) Assignee: UNIVERSITY OF SOUTHAMPTON, Southampton (GB)

( * ) Notice: Subject to any disclaimer, the term of this patent is extended or adjusted under 35 U.S.C. 154(b) by 137 days.

(21) Appl. No.: 16/644,601

(22) PCT Filed: Sep. 6, 2018

(86) PCT No.: PCT/GB2018/052522
§ 371 (c)(1),
(2) Date: Mar. 5, 2020

(87) PCT Pub. No.: WO2019/048860
PCT Pub. Date: Mar. 14, 2019

(65) Prior Publication Data
US 2020/0383809 A1 Dec. 10, 2020

(30) Foreign Application Priority Data

Sep. 6, 2017 (GB) ...................................... 1714337

(51) Int. Cl.
*A61F 2/82* (2013.01)
*A61F 2/04* (2013.01)
(Continued)

(52) U.S. Cl.
CPC .................. *A61F 2/82* (2013.01); *A61F 2/04* (2013.01); *A61M 25/007* (2013.01);
(Continued)

(58) Field of Classification Search
CPC .............................. A61F 2/04; A61F 2002/041
(Continued)

(56) References Cited

U.S. PATENT DOCUMENTS 2,972,779 A 2/1961 Cowley
5,052,998 A * 10/1991 Zimmon ............... A61M 25/04
604/8
(Continued)

FOREIGN PATENT DOCUMENTS

DE 20 2006 017068 U1 8/2007
EP 3 184 140 A1 6/2017
(Continued)

OTHER PUBLICATIONS

International Search Report and Written Opinion issued in International Application No. PCT/GB2018/052522 dated Dec. 7, 2018; 13 pages.
(Continued)

*Primary Examiner* — Suzette J Gherbi
(74) *Attorney, Agent, or Firm* — Wegman Hessler

(57) ABSTRACT

A stent (100) comprising a stent wall (102), the stent wall (102) having a plurality of side holes (110) extending therethrough, each side hole (110) having an upstream end (116) and a downstream end (118). The stent wall (102) tapers in thickness in a direction towards the side hole (110) at the upstream (116) and/or downstream (118) end of at least one of the side holes (110). Also disclosed are methods for making side holes (110) in stents (100) by milling and making stents (100) having side holes (110) by injection moulding.

19 Claims, 7 Drawing Sheets

(51) Int. Cl.
*A61M 25/00* (2006.01)
*A61M 27/00* (2006.01)

(52) U.S. Cl.
CPC ...... *A61M 25/0015* (2013.01); *A61M 27/008* (2013.01); *A61F 2002/048* (2013.01); *A61F 2240/001* (2013.01); *A61F 2250/0036* (2013.01)

(58) Field of Classification Search
USPC .............................................. 623/23.64–23.7
See application file for complete search history.

(56) References Cited

U.S. PATENT DOCUMENTS

| | | | |
|---|---|---|---|
| 5,180,387 A | | 1/1993 | Ghajar et al. |
| 6,228,111 B1 * | | 5/2001 | Tormala .................. A61F 2/04 424/426 |
| 8,597,367 B2 * | | 12/2013 | Dillinger ............. A61M 27/008 623/23.7 |
| 9,789,282 B2 * | | 10/2017 | McKinnon ........ A61M 25/0015 |
| 2008/0124373 A1 * | | 5/2008 | Xiao ..................... A61L 31/086 424/423 |
| 2008/0249457 A1 * | | 10/2008 | Li ........................ A61M 27/00 604/8 |
| 2009/0187254 A1 | | 7/2009 | Deal |
| 2009/0319026 A1 * | | 12/2009 | Meyer .................... A61F 2/915 623/1.16 |
| 2011/0070357 A1 * | | 3/2011 | Mitchell ................. A61L 31/16 427/2.25 |
| 2011/0196507 A1 * | | 8/2011 | St. Pierre .......... A61M 25/0009 623/23.66 |
| 2012/0010721 A1 * | | 1/2012 | Dillinger ............. A61M 27/008 623/23.7 |
| 2012/0290100 A1 * | | 11/2012 | Li ....................... A61M 27/008 623/23.66 |
| 2013/0199713 A1 * | | 8/2013 | Zamponi ................... A61F 2/82 156/247 |
| 2015/0088090 A1 | | 3/2015 | Macy, Jr. |
| 2015/0208982 A1 * | | 7/2015 | Ho ............................ A61P 9/10 264/154 |
| 2015/0223953 A1 * | | 8/2015 | Pendleton ............... A61F 2/852 623/23.68 |
| 2015/0258303 A1 | | 9/2015 | Triel et al. |
| 2016/0045347 A1 * | | 2/2016 | Smouse .................... A61F 2/95 623/23.66 |

FOREIGN PATENT DOCUMENTS

FR  2 611 486 A1  9/1988
GB  2152382 A  8/1985

OTHER PUBLICATIONS

Search Report issued in Application No. GB1714337.1 dated Feb. 21, 2018; 4 pages.

* cited by examiner

STENT WITH STREAMLINED SIDE HOLES

CROSS REFERENCE TO RELATED APPLICATION

This application claims the priority filing benefit of International Patent Application No. PCT/GB2018/052522 filed Sep. 6, 2018, and United Kingdom Patent Application No. GB1714337.1 filed on Sep. 6, 2017, which are incorporated herein by reference in their entirety.

FIELD OF THE INVENTION

This invention relates to stents, in particular ureteric stents, having side holes. The invention also relates to methods for the fabrication of such stents.

BACKGROUND

Ureteric stents are thin tubes inserted into the ureter in order to allow for urine drainage in the presence of a ureteric obstruction. They are typically 20 to 30 cm long and have multiple circular holes across the stent wall, which permit flow exchange between the central bore of the stent and the surrounding environment.

Ureteric stents are largely employed in the clinics to retrieve urine drainage in either cases of externally- or internally-induced occlusion of the ureter lumen, for example caused by a tumour mass or a kidney stone. The stent provides a pathway for urine flow to bypass the occlusion, lowering the static pressure within the kidneys and reducing the risk of renal tissue damage.

The use of ureteric stents is, however, associated with a range of side effects and complications. The most common source of stent dysfunction is the deposition and growth of encrusting and bacterial deposits over the stent surface, which can cause blockage of the side holes and the bore of the stent. This compromises urine drainage and can result in increased renal pelvic pressure, which may have severe consequences for the patient, and often requires surgical re-intervention or pharmaceutical treatment, with significant impact on healthcare costs and patients' quality of life.

Although different strategies have been proposed to reduce the impact of encrustation on stent lifetime, with the majority focusing on the introduction of novel bulk materials and surface coatings, encrustation of ureteric stents is still recognised as a major cause of stent failure and associated side effects on patients.

There is currently a move towards the use of metallic stents as a more reliable product against encrustation and erosion (particularly for long-term placement). However, metallic stents are more expensive to fabricate than the more commonly used polymer- or silicone-based stents.

Other approaches against encrustation have focussed on surface coatings, such as heparin (*J Endourol.*, 22(3):465-472, 2008) and carbon-based (*J Urol.*, 177(5):1923-1927, 2007) coatings, which have demonstrated success in reducing the rate of encrustation.

Notably, the introduction of new material or coating strategies into the industrial and clinical environments is often hindered by high associated costs and technological complexity. For instance, metal stents have been proposed since the late '90s as a means to reduce the occurrence of mineralogical encrustation (as opposed to the more common polymer- or silicone-based stents), but they have not yet become a widespread practice in the clinic.

It has been observed that encrustation of stents can be more pronounced at the location of the side holes. Consequently, it has been suggested that side holes represent one of the initial anchoring sites for encrusting material.

Tong et al. have reported a computational fluid dynamics (CFD) study on a new side hole design, which comprises tubular extrusions of the side holes with the purpose of providing more efficient urine drainage (*J Biomech. Eng.*, 129(2):187-192, 2006). This design has the potential disadvantage of increasing patient discomfort due to the contact between the extrusions and the inner ureter wall. The extrusions are also more prone to mechanical breakage, which is potentially made worse by encrustation or other chemical factors. Such stents are also relatively complicated to fabricate.

There is therefore a need for a stent design that effectively reduces encrustation without significantly impacting on production complexity or costs, which is independent of the bulk material from which the stent is made or of any surface treatments or coatings, and which mitigates against the disadvantages of currently known stents.

SUMMARY OF THE INVENTION

The invention provides a stent comprising a stent wall having an inner surface and an outer surface, wherein the inner surface of the stent wall defines a central bore. The stent wall has a plurality of side holes extending therethrough. Each side hole may be defined by a surrounding side hole wall that extends between the inner and outer surfaces of the stent wall. Each side hole has an upstream end and a downstream end, spaced apart in the direction of, or along, the longitudinal axis of the stent, and the stent wall tapers so that it decreases in thickness in a direction towards the side hole at the upstream and/or downstream end of at least one of the side holes.

The stent wall may taper away from both the inner surface and the outer surface of the stent wall at the upstream and/or downstream end of the side hole.

The stent wall may taper in thickness (for example, as viewed in cross-section in any of the planes described herein) to form a vertex located between, and offset in the radial direction of the stent from, both the inner surface and the outer surface of the stent wall. For example, the stent wall may taper symmetrically so that the vertex is located half way between the inner surface and outer surface of the stent wall. Alternatively, the stent wall may taper asymmetrically so that the vertex is offset in the radial direction from the midpoint between the inner and outer surfaces of the stent wall. The vertex may have an internal angle of 30 to 120°, 30 to 90°, 40 to 60°, 40 to 50°, for example about 45°.

The stent wall may taper away from the inner surface of the stent wall but not taper away from the outer surface of the stent wall at the upstream end of the at least one of the side holes. Alternatively, the stent wall may taper away from the outer surface of the stent wall but not taper away from the inner surface of the stent wall at the upstream end of the at least one of the side holes. The side hole wall may meet the inner or outer surface of the stent wall to form a non-perpendicular vertex.

The stent wall may taper away from the inner surface of the stent wall but does not taper away from the outer surface of the stent wall at the downstream end of at the at least one of the side holes. Alternatively, the stent wall may taper away from the outer surface of the stent wall but not taper away from the inner surface of the stent wall at the downstream end of at the at least one of the side holes. The side hole wall may meet the inner or outer surface of the stent wall to form a non-perpendicular vertex.

The stent wall may be tapered in a direction towards the side hole around the entire perimeter of the side hole. Alternatively, the stent wall may be tapered only at the upstream and/or downstream end regions of the side hole, or in the vicinity of the upstream and downstream end regions of the side hole. For example, the stent wall may be tapered at an angle of ±45°, ±30°, or ±15° either side of the upstream and/or downstream end of the side hole. Alternatively, the side hole may be tapered only at the extreme upstream and/or downstream ends of the side hole.

The side hole may extend through the stent wall at an oblique angle relative to the longitudinal axis of the stent. The side hole may extend through the stent wall at an angle of 20 to 85°, 30 to 80°, 30 to 70°, 30 to 60°, 35 to 55°, 40 to 50°, for example about 45° relative to the longitudinal axis of the stent. For example, the longitudinal axis of the side hole may extend through the stent wall at an oblique angle to the longitudinal axis of the stent.

The stent may have an upstream plurality of side holes in an upstream portion of the stent and a downstream plurality of side holes in a downstream portion of the stent, wherein the upstream plurality of side holes extend through the stent wall at an acute angle relative to the longitudinal axis of the stent when measured from the upstream direction, and wherein the downstream plurality of side holes extend through the stent wall at an obtuse angle relative to the longitudinal axis of the stent when measured from the upstream direction. More generally, the upstream plurality of side holes may be arranged to direct fluid into the central bore of the stent, and the downstream plurality of side holes may be arranged to direct fluid out from the central bore of the stent.

The side holes in which the stent wall tapers in thickness in a direction towards the side hole at the upstream and/or downstream end of the side holes may be confined to the upstream end of the stent.

The stent wall may taper in a linear manner. For example, the stent wall may taper at an approximately constant rate in a direction towards the side hole.

The stent wall may taper at a non-constant rate. For example, the stent wall may taper to form a convex side hole wall when viewed in cross-section.

Each of the plurality of side holes may have a minimum diameter in the direction of the longitudinal axis of the stent of 0.5 to 3.0 mm, 0.5 to 1.0 mm, 0.6 to 0.9 mm, or 0.7 to 0.8 mm, in particular about 0.75 mm.

The main, non-tapered part of the stent wall may have a thickness of 0.2 to 1.0 mm, or 0.2 to 0.4 mm, in particular about 0.3 mm.

The invention also provides a method of making a side hole in a stent wall, wherein the method comprises cutting a side hole in the stent wall by milling, in particular by micro-milling.

The side hole may be milled in a stepwise process using a milling tool. The milling tool may be removed from the stent between each step.

One (a first) step of the stepwise process may form one (a first) portion of the stent side hole (e.g. a portion of the side hole side wall) and another (second or further) step of the stepwise process may form a different (second or further) portion of the side hole (e.g. a portion of the side hole side wall).

Each step of the stepwise process may comprise moving the stent and/or the milling tool to cause relative rotation of the milling tool about the longitudinal (central) axis of the resulting side hole.

The longitudinal axis of the resulting side hole may be substantially perpendicular to the longitudinal axis of the portion of the stent in which the side hole is formed.

The method may further comprise inserting a support or support material into the central bore of the stent. The support may support the stent wall during the milling (or cutting) of the side hole.

The method may further comprise cooling the stent prior to milling, for example to a temperature of −130° C. or less, or −180° C. or less, for example to about −196° C. The stent may be cooled sufficiently to prevent the stent from flexing when milled. For example, the stent may be cooled to ensure that the stent material has a Young's modulus of at least 2 GPa, at least 3 GPa, at least 4 GPa, or at least 5 GPa, for example about 5 GPa, when milled.

The stent may be cooled using liquid nitrogen. For example, the stent may be cooled by immersion in liquid nitrogen.

The invention also provides a method of making a stent having side holes, wherein the method comprises making the stent by injection moulding.

The mould used in the injection moulding process may be an aluminium mould. The mould may also be an iron, magnesium, or a copper mould.

The injection moulding method may comprise the step of removing the stent from the mould by dissolving the mould in acid. The acid may be hydrochloric acid and/or nitric acid.

The mould may be formed by 3D printing. The mould may be 3D printed from a polymer and then subsequently coated in aluminium. Alternatively, the mould may be 3D printed directly from aluminium.

The stent may be made from silicone or a silicone-based material. Alternatively, the stent may be made from a polymer or from a metal.

The stent may be a ureteric stent. Alternatively, the stent may be suitable for use in other parts of the body, such as the brain, the biliary, or pancreatic system. Alternatively, the invention may apply to a catheter instead of a stent.

DETAILED DESCRIPTION OF THE INVENTION

The following description and examples are intended to illustrate a number of non-limiting embodiments of the invention. Unless otherwise stated, any of the features disclosed herein may be combined insofar as the relevant features are compatible. The disclosure of certain features in combination in reference to the specific examples described herein does not imply that all of the features in question must necessarily be present together.

Figure 1:
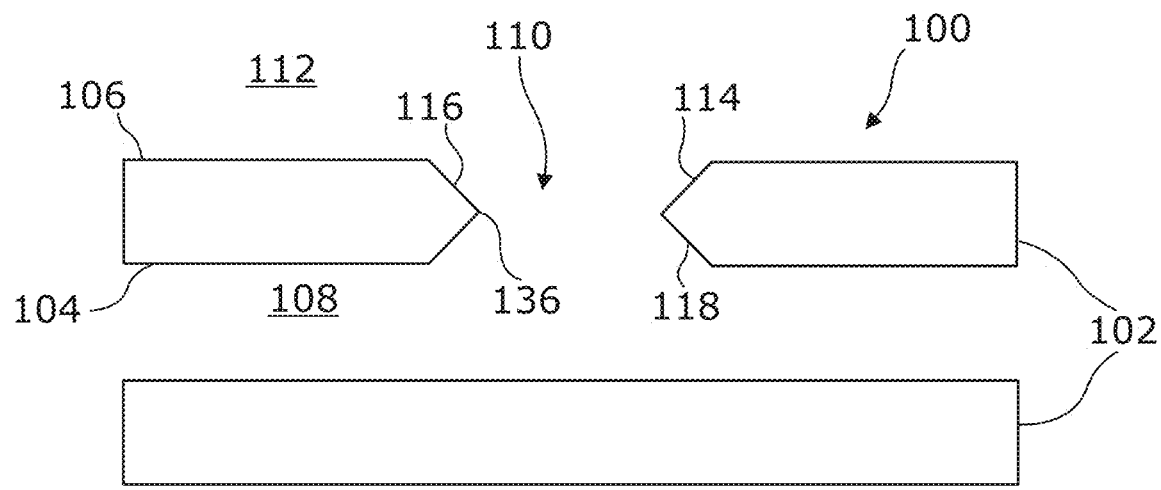
FIG. 1 illustrates a cross-section taken along the longitudinal axis of a portion of a stent according to the present invention.

Referring to FIG. 1, the stent 100 comprises a stent wall 102 having an inner 104 surface and an outer surface 106. The inner surface 104 of the stent wall 102 defines a central bore 108 of the stent 100, through which fluid, such as urine, may flow. The stent 100 comprises a plurality of side holes 110 that extend through the stent wall 102 from the inner surface 104 to the outer surface 106 to provide fluid communication between the central bore 108 of the stent 100 and the surrounding environment 112. Each side hole is defined by a surrounding side hole wall 114 that extends between the inner 104 and the outer 106 surfaces of the stent wall 102. The stent wall 102 tapers in thickness in a direction towards the side hole 110 at the upstream end 116 and the downstream end 118 of the side hole 110. The thickness of the stent wall 102 is the distance between the innermost and the outermost surfaces of the stent wall (e.g. the inner 104 and outer 106 surfaces of the stent wall 102) in a direction perpendicular to the longitudinal axis of the stent 100. The thickness is typically measured in a radial direction from the longitudinal axis of the stent 100. The stent wall 102 may taper to reduce in thickness in a direction towards the centre of the side hole 110 or generally towards the side hole 110 when viewed in the relevant cross-section plane, parallel to a radial direction from the longitudinal axis of the stent 100. In other words, the stent wall 102 tapers immediately adjacent to the side hole 110. In this way, the surface of the tapered portion of the stent wall 102 defines at least a portion of the side hole wall 114.

As used herein, the upstream end is the end from which fluid (e.g. urine) flows, and the downstream end is the end towards which the fluid flows when the stent 100 is in use.

The upstream end and the downstream end of the stent or of the side holes 110 may be identical in structure and will therefore be indistinguishable and interchangeable, as in FIG. 1. Alternatively, the upstream 116 and the downstream 118 ends of the side holes 110 may be structurally distinct. The stent 100 has a longitudinal axis, which extends along the centre of the central bore 108 from the upstream end of the stent to the downstream end of the stent when the stent is arranged in a linear configuration.

The cross-section of the part of the stent wall 102 that defines the upstream 116 or downstream 118 end of the side hole 110 may taper, to become progressively narrower, in a direction towards the centre of the side hole 110. The cross-section may be taken in a plane defined by the longitudinal axis of the side hole 110 (i.e. along the central axis of the side hole 110) and the longitudinal direction of the stent 100, i.e. the longitudinal axis of the side hole 110 lies in the cross-section plane and the cross-section plane is parallel to the longitudinal axis of the stent 100. At least a portion of the side hole wall 114 (e.g. when viewed in this cross-section plane) at the upstream 116 and/or downstream 118 ends of the side hole 110 may be at an oblique angle to the longitudinal axis of the stent 100.

Figure 2:
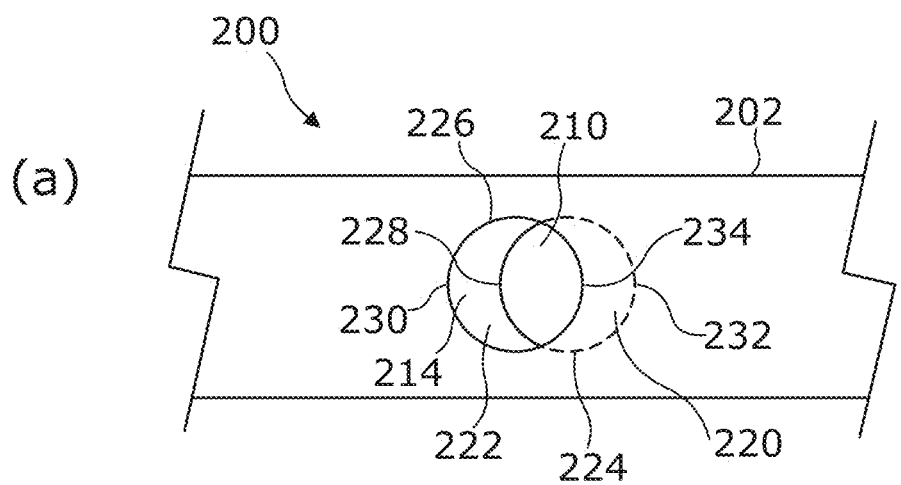
FIG. 2(a) illustrates a top-down plan view of a portion of a stent according to the present invention.
FIG. 2(b) illustrates a top-down plan view of a portion of a stent according to the present invention.
Figure 2:
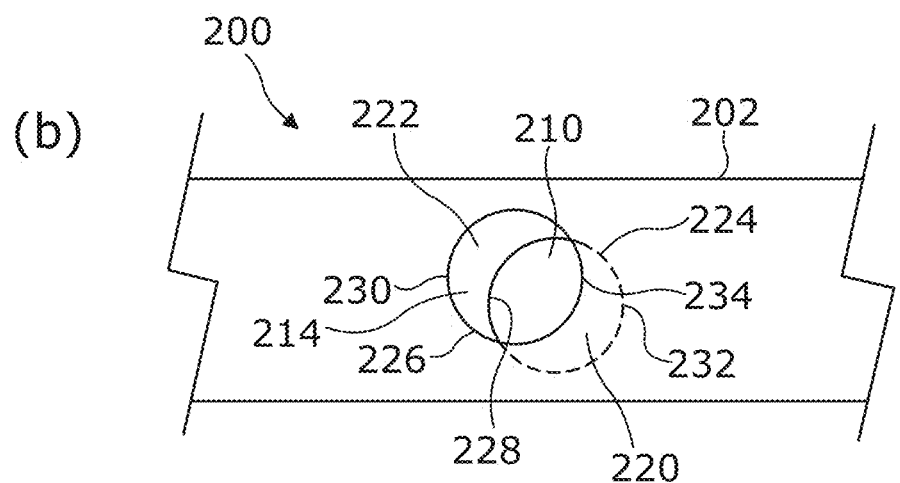

Referring to FIGS. 2(a) and 2(b), the side hole 210 extends through the stent wall 202 to form an internal opening 220 in the inner surface of the stent wall and an external opening 222 in the outer surface of the stent wall 202. Each of the internal 220 and external 222 openings may have a point around its perimeter 224, 226 that is the closest to the upstream end of the stent, i.e. the extreme upstream point 228, 230 of the opening 220, 222. Similarly, each of the internal 220 and external 222 openings may have a point around its perimeter 224, 226 that is the closest to the downstream end of the stent, i.e. the extreme downstream point 232, 234 of the opening 220, 222.

Typically, the side hole 210 will be symmetrical with respect to reflection in a plane defined by (i.e. containing) a radial direction from the longitudinal axis and the longitudinal axis itself, as shown in FIG. 2(a). In this case, the extreme upstream 228, 230 and downstream 232, 234 points of the internal 220 and external 222 openings will lie in this plane. However, this may not be so, for example the internal 220 and external 222 openings may be offset around the circumference of the stent wall 202, as shown in FIG. 2(b). In this case, it is useful to consider a different frame of reference.

For example, at least a portion of the side hole wall 214 at the downstream end of the side hole 210 may be at an oblique angle to the longitudinal axis of the stent 200 when viewed in cross-section in a plane defined by: i) the vector that connects the extreme downstream points 232, 234 of the internal 220 and external 222 openings, and ii) the longitudinal direction of the stent 200. In other words, the vector that connects the extreme downstream points 232, 234 of the internal 220 and external 222 openings lies in the cross-section plane and the cross-section plane is parallel to the longitudinal axis of the stent 200.

Similarly, at least a portion of the side hole wall 214 at the upstream end of the side hole 210 may be at an oblique angle to the longitudinal axis of the stent 200 when viewed in cross-section in a plane defined by: i) the vector that connects the extreme upstream points 228, 230 of the internal 220 and external 222 openings, and ii) the longitudinal direction of the stent 200. In other words, the vector that connects the extreme upstream points 228, 230 of the internal 220 and external 222 openings lies in the cross-section plane and the cross-section plane is parallel to the longitudinal axis of the stent 200.

The oblique angle of the stent wall may be 20 to 85°, 30 to 80°, 30 to 70°, 30 to 60°, 35 to 55°, 40 to 50°, for example about 45° relative to the longitudinal axis of the stent 200. Substantially all of the side hole wall 214 at the upstream and/or downstream end of the side hole may be at an oblique angle relative to the longitudinal axis of the stent 200. Alternatively, at least 10%, at least 20%, at least 30%, at least 40%, at least 50%, at least 60%, at least 70%, at least 80%, at least 90%, or the entire height of the side hole wall 214, as measured in the direction perpendicular to the longitudinal axis of the stent 200 in the relevant cross-section plane, may be at an oblique angle to the longitudinal axis of the stent 200.

Returning to FIG. 1, the stent wall 114 may taper inwardly away from both the inner surface 104 and the outer surface 106 of the stent wall 102 at the upstream 116 and downstream 118 ends of a side hole 110, as illustrated in FIG. 1. In this context, inwardly away from means radially towards the opposing surface of the stent wall 102. For example, the outer surface 106 of the stent wall 102 may deflect towards the inner surface 104 of the stent wall 102 to form the side hole wall 114, and vice versa.

The stent wall 102 may taper in thickness to form a vertex 136 located between, and offset in the radial direction from, both the inner surface 104 and the outer surface 106 of the stent wall 102. The vertex 136 may be located half way between the inner surface 104 and outer surface 106 of the stent wall 102. The vertex 136 may have an internal angle, defined as the angle between the converging portions of the side hole wall 114 that form the vertex 136, of 30 to 120°, 30 to 90°, 40 to 60°, 40 to 50°, for example about 45°, which has been found to be advantageous for reducing encrustation.

The stent wall 102 may taper inwardly away from both the inner 104 and the outer 106 surfaces to an equal extent. For example, the cross-section of the side hole wall 114 may be symmetrical with respect to reflection about the line defining the mid-point between the inner 104 and outer 106 surfaces of the stent wall 102. For example, the tapered section of the stent wall 102 may form an isosceles or equilateral triangle in cross-section, wherein the base of the triangle faces away from the side hole 110.

Alternatively, the stent wall 102 may taper asymmetrically so that the vertex 136 is offset in the radial direction from the midpoint between the inner 104 and outer 106 surfaces of the stent wall 102. For example, the tapered section of the stent wall 102 may form an acute scalene triangle in cross-section.

Instead of forming a vertex 136, the portions of the side hole wall 114 that lie at an oblique angle to the longitudinal axis of the stent 100 due to the tapering of the stent wall 102 may be joined by a portion of the side hole wall 102 that is perpendicular to the longitudinal axis of the stent 100.

When in use, for example when inserted into the ureter of a patient, the stent 100 provides a fluid pathway around an occlusion, such as a kidney stone or caused by a cancerous growth. The stent 100 typically has side holes 110 located along its length and located either side of the occlusion when in use. On the upstream side of the occlusion, fluid may pass into the central bore 108 of the stent 100 from the surrounding environment 112. In the case of a ureteric stent the surrounding environment 112 is the intraluminal region of the ureter. The occlusion blocks or obstructs the passage of urine through the ureter, which results in an increase in pressure within the intraluminal region of the ureter. This causes fluid to pass into the central bore 108 of the stent 100 through the side holes 110 that are in close proximity to the occlusion on the upstream side of the occlusion. The urine bypasses the occlusion through the central bore 108 of the stent. Once the urine has passed the occlusion, the increased pressure within the central bore 108 of the stent 100 causes urine to flow out of the central bore 108 of the stent 100 through the side holes 110 that are on the downstream side of the occlusion.

As a result, only relatively few of the side holes 110 are active in transferring fluid between the central bore 108 of the stent 100 and the surrounding environment 112, these being the side holes 110 in close proximity to the occlusion. The majority of the side holes 110 experience relatively small amounts of fluid exchange, which results in regions of flow stagnation within the side holes 110. This flow stagnation causes the build-up of encrusting deposits within the side holes 110, such as bacterial or crystal deposits, which results in the blockage or obstruction of the side holes 110 and provides anchor points, or nucleation points, for further encrustation or biofilm formation.

Figure 3:
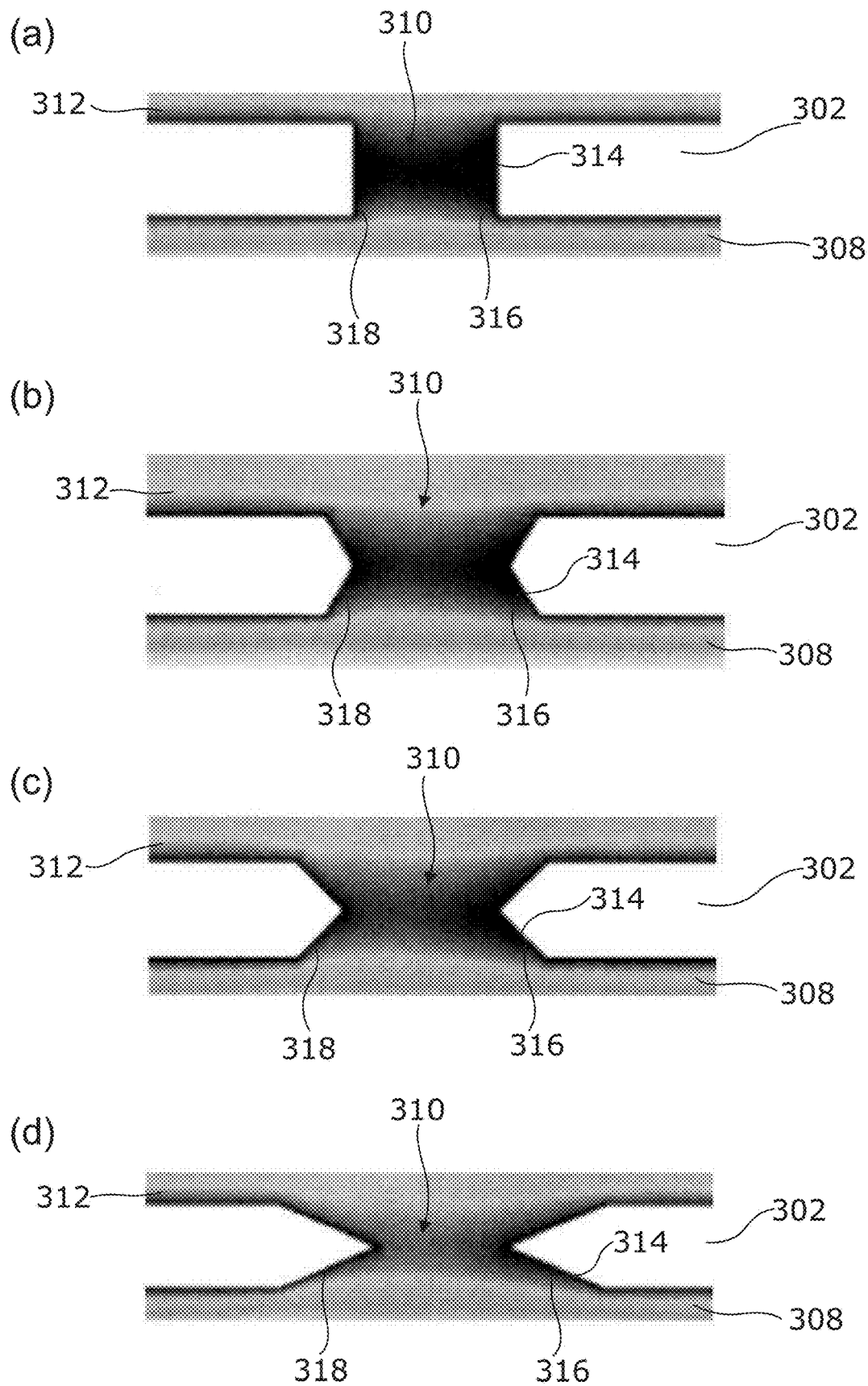
FIG. 3(a) illustrates a cross-section taken along the longitudinal axis of a portion of a stent wall of a stent not according to the present invention and showing the flow velocity of the fluid within and surrounding the stent.
FIG. 3(b) illustrates a cross-section taken along the longitudinal axis of a portion of a stent wall of a stent according to the present invention having an internal vertex angle of 120° and illustrates the flow velocity of the fluid within and surrounding the stent.
FIG. 3(c) illustrates a cross-section taken along the longitudinal axis of a portion of a stent wall of a stent according to the present invention having an internal vertex angle of 90° and illustrates the flow velocity of the fluid within and surrounding the stent.
FIG. 3(d) illustrates a cross-section taken along the longitudinal axis of a portion of a stent wall of a stent according to the present invention having an internal vertex angle of 45° and illustrates the flow velocity of the fluid within and surrounding the stent.

Referring to FIG. 3(a), conventional ureteric stents have side holes 310 that are punched through the side walls 302 in a perpendicular direction to the longitudinal axis of the stent. This results in the side holes 310 having side hole walls 314 that are perpendicular to the longitudinal axis of the stent when viewed in cross-section. The grayscale shading surrounding the stent wall in FIGS. 3(a)-(d) illustrates the flow velocity: the darker the shading the slower the flow velocity. As can be seen, the region within the side hole 310 experiences substantially reduced flow velocity and stagnation compared to the fluid in the central bore 308 of the stent and the surrounding environment 312. This allows the accumulation of encrusting deposits within the side hole 310, ultimately leading to blockage of the side hole 310 and failure of the stent.

As can be seen in FIGS. 3(b)-(d), the stents according to the present invention reduce the flow stagnation due to the more streamlined shape of the side holes 310 in the flow direction resulting from the tapered profile of the stent wall 302 at the upstream 316 and/or downstream 318 ends of the side holes 310.

Figure 4:
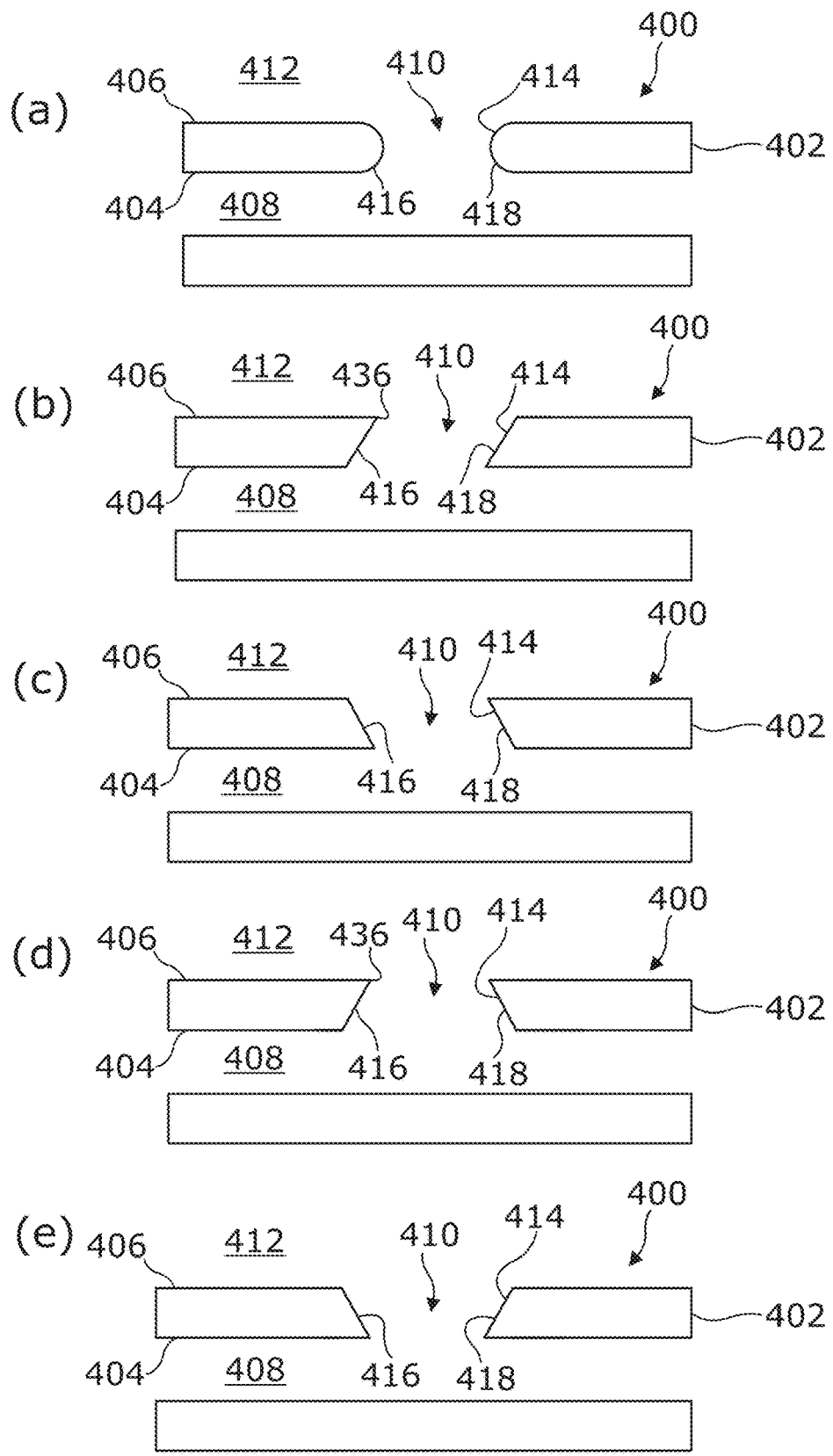
FIG. 4 illustrates cross-sections taken along the longitudinal axis of portions of various stents according to the present invention.

Referring to FIG. 4(a), the side hole walls 414 may instead taper to form a rounded, or convex, profile when viewed in cross-section. This is one example of the stent wall 402 tapering at a non-constant rate.

Referring to FIG. 4(b), the stent wall 402 may taper away from the inner surface 404 of the stent wall 402 but not taper away from the outer surface 406 of the stent wall 402 at the upstream end 416 of the side hole 410 and may taper away from the outer surface 406 of the stent wall 402 but not taper away from the inner surface 404 of the stent wall 402 at the downstream end 418 of the at side hole 410. In this way, fluid that flows in a downstream direction is directed from the central bore 408 of the stent 400 to the surrounding environment 412, e.g. the intraluminal region of the ureter.

Alternatively, referring to FIG. 4(c) the stent wall 402 may taper away from the outer surface 406 of the stent wall 402 but not taper away from the inner surface 404 of the stent wall 402 at the upstream end 416 of the side hole 410 and may taper away from the inner surface 404 of the stent wall 402 but not taper away from the outer surface 406 of the stent wall 402 at the downstream end 418 of at the side hole 410. In this way, fluid that flows in a downstream direction is directed from the surrounding environment 412, e.g. the intraluminal region of the ureter, into the central bore 408 of the stent 400.

The upstream 416 and the downstream 418 ends of the side hole wall 414 may be parallel to each other, as illustrated in FIGS. 4(b) and 4(c).

One or more of the side holes 410 may extend through the stent wall 402 at an oblique angle relative to the longitudinal axis of the stent 400. This would result in a cross-section of the sort illustrated in FIGS. 4(b) and 4(c). For example, the side hole 410 may extend through the stent wall at an angle of 20 to 85°, 30 to 80°, 30 to 70°, 30 to 60°, 35 to 55°, 40 to 50°, for example about 45° relative to the longitudinal axis of the stent 400. For example, the longitudinal axis of the side hole 410 may extend through the stent wall 402 at an oblique angle to the longitudinal axis of the stent 400. The side hole 410 may be tubular and may have a substantially circular cross-section when viewed along its longitudinal axis (i.e. along its length).

Referring to FIG. 4(d), the stent wall 402 may taper away from the inner surface 404 of the stent wall 402 but not taper away from the outer surface 406 of the stent wall 402 at both the upstream 416 and downstream 418 ends of the side hole 410. Alternatively, referring to FIG. 4(e), the stent wall 402 may taper away from the outer surface 406 of the stent wall 402 but not taper away from the inner surface 404 of the stent wall 402 at both the upstream 416 and downstream 418 ends of the side hole 410.

It should also be noted that, in general, it is not necessary for both the upstream 416 and the downstream 418 ends to both taper. For example, one or the other of the upstream 416 or downstream 418 ends of the side holes 410 may not taper.

The portion of the side hole wall 402 that is at an oblique angle to the longitudinal axis of the stent 400 may meet the inner 404 or outer surface 406 of the stent wall 402 to form a vertex 436. Alternatively, the oblique portion of the side hole wall 414 may be joined to either the inner 404 or the outer 406 surface of the stent wall 402 by an untapered portion, for example that is perpendicular to the longitudinal axis of the stent 400.

The stent wall 402 may be tapered in a direction towards the side hole 410, for example in a direction towards the centre of the side hole 410, around the entire perimeter of the side hole 410. Alternatively, the stent wall 402 may be tapered only at the upstream and/or downstream end regions of the side hole 410, or in the vicinity of the upstream and downstream end regions of the side hole 410. For example, the stent wall may be tapered at an angle of ±45°, ±30°, or ±15° either side of the upstream 416 and/or downstream 418 end of the side hole 410. Alternatively, the side hole 410 may be tapered only at the extreme upstream 416 and/or downstream 418 ends of the side hole 410.

The side hole wall 414 at the upstream 416 and/or downstream 418 end of the side hole 410 may be at an oblique angle to the longitudinal axis of the stent 400 (due to the tapering of the stent wall 402) along its entire height, or along at least 10%, at least 20%, at least 30%, at least 40%, at least 50%, at least 60%, at least 70%, at least 80%, at least 90% of its height, where the height of the side hole 410 is the distance between the inner 404 and outer 406 surfaces of the stent wall 402 and is in a direction perpendicular to the longitudinal axis of the stent 400. Generally, this will be in a radial direction.

The stent wall 402 may taper at the upstream 416 and/or downstream 418 end of the side hole over a length that is at least 20%, at least 30%, at least 40%, or at least 50% of the thickness of the main, non-tapered portion of the stent wall 402. The length is measured parallel to the longitudinal axis of the stent 400.

Each of the plurality of side holes 410 may have a minimum diameter in the direction of the longitudinal axis of the stent 400 of 0.5 to 3.0 mm, 0.5 to 1.0 mm, 0.6 to 0.9 mm, or 0.7 to 0.8 mm, in particular about 0.75 mm. For example, the side holes 110 may have a diameter (for example a minimum or maximum diameter, e.g. in the direction of the longitudinal axis of the stent) of less than 1 cm, or of less than 1 mm (i.e. sub-millimetre, or micron-sized). The diameter in question may be, for example, the diameter of the internal or external opening. For example, the side holes 110 may have a diameter in the range of about 500 μm to about 800 μm.

The stent wall 402 may have a thickness of 0.2 to 1.0 mm, or 0.2 to 0.4 mm, for example about 0.3 mm in the non-tapered regions.

The side holes 410 may all be of the same type or may have the same cross-section. For example, each of the plurality side holes 410 may have a cross-section as shown in FIG. 1. Alternatively, the stent may comprise a number of side holes 410 of different geometries. For example, the stent 400 may comprise an approximately equal number of the side holes 410 illustrated in FIGS. 4(b) and 4(c). For example, the ratio of the two different types of side hole 410 may be at most 1.2:1, or at most 1.1:1. The two different types of side hole 410 projecting in opposite directions along the longitudinal axis of the stent 400 may alternate along the length of the stent 400 to equalise the exchange of fluid between the central bore 408 of the stent 400 and the surrounding environment 412. Alternatively, the upstream portion of the stent may have side holes 410 as illustrated in FIG. 4(c) (i.e. directing fluid into the central bore 408 of the stent) and the downstream portion of the stent 400 may have side holes 410 as illustrated in FIG. 4(b) (i.e. directing fluid out from the central bore 408 of the stent 400). Preferably, the side holes 410 illustrated in FIG. 4(c) will be located on the upstream side of the occlusion when the stent 400 is in use, for example in the upstream half of the stent 400, and the side holes 410 illustrated in FIG. 4(b) will be located on the downstream side of the occlusion, for example in the downstream half of the stent 400. The transition point along the length of the stent 400 at which the side holes 410 change from being those illustrated in FIG. 4(c) to those illustrated in FIG. 4(b) may be the mid-point along the length of the stent 400. Alternatively, the location of the occlusion may be determined and the transition point may be selected so that the side holes 410 illustrated in FIG. 4(c) will be located on the upstream side of the occlusion when the stent 400 is in use, and the side holes 410 illustrated in FIG. 4(b) will be located on the downstream side of the occlusion.

The tapered side holes 410 may be distributed along the entire length of the stent 400. Alternatively, the tapered side holes 410 may be located only along the part of the stent 400 that will be located in the upper or proximal part of the ureter when the stent 400 is in use, i.e. the upstream portion of the stent. For example, the tapered side holes 410 may be confined to one end of the stent 400, preferably the upstream end of the stent 400 that is located in the proximal part of the ureter when in use. The proximal part of the ureter has a larger diameter, which reduces the flow velocity. The upstream end of the stent 400 is therefore more prone to the deposition of encrusting deposits. The use of streamlined side holes 410 in the upstream part of the stent 400 is therefore particularly advantageous. Limiting the extent of the streamlined side holes 410 to only the upstream part of the stent 400 simplifies the manufacture of the stent 400 and reduces its cost, while maintaining a significant benefit. The streamlined side holes 410 may be located within a region extending no further from one end of the stent 400 (preferably the upstream end of the stent 400 if the upstream and downstream ends of the stent 400 are structurally distinct) than 40%, 30%, or 20% of the total length of the stent 400. For example, the streamlined side holes 410 may be located within a region extending no further than 12 cm, 9 cm, or 6 cm along the length of the stent 400 from one of its ends, preferably the upstream end of the stent 400.

Stents 400 in accordance with the present invention may be formed from any suitable material because it is the streamlined shape of the side holes 410 that results in the reduction in encrustation, not any specific material or coating properties. For example, the stent 400 may be made from silicone or a polymer-based material, for example polyurethane or polyethylene. Alternatively, the stents 400 could be made from a metal, such as a nickel-cobalt-chromium-molybdenum alloy.

Fabrication

The side holes 110 may be formed in the stent wall 102 by milling, in particular by micro-milling. Micro-milling may involve milling using milling tools having micron-sized cutting surfaces, for example to form micron-sized features, such as micron-sized side holes 110. Computer numerical control (CNC) milling is particularly advantageous due to its accuracy and ability to form complex shapes. Side holes 110 other than those of the present invention (i.e. those without tapered side walls 114) may also be formed by milling.

Typically, stent side holes 110 are punched into the stent wall 102. However, it is difficult to accurately control the shape and profile of the side holes 110 by punching. Furthermore, the side holes 110 may have a diameter on the micrometre or millimetre scale. For example, the side holes 110 may have a diameter (for example a minimum or maximum diameter) of less than 1 cm, or of less than 1 mm (i.e. sub-millimetre, or micron-sized). The diameter in question may be, for example, the diameter of the internal or external opening. For example, the side holes 110 may have a diameter in the range of about 500 µm to about 800 µm. However, punching does not provide the level of control or resolution required to manufacture sub-millimetre side holes 110 accurately.

Various other methods of fabricating stents 100 having side holes 110 are possible, such as laser cutting, water-jet cutting, and micro-milling. However, micro-milling has been found to be the most suitable, accurate and reliable method for forming micron-sized side holes 110 in stents 100. For example, laser cutting was found to cause undesirable deformation of the cut zone and melting of surrounding material, precluding the formation of carefully shaped side holes 110. Water-jet cutting was found to require additional drilling steps prior to the water-jet cutting in order to cut holes 110 with diameters smaller than the substrate (i.e. stent wall 102) thickness.

Various shaped milling tools may be used to form the various shaped side holes 110, 410 according to the present invention. For example, an end mill 500, such as the cylindrical end mill 500 illustrated in profile in FIG. 5(a), may be used to bore side holes 410 through the stent wall 402 at an oblique angle to the longitudinal axis of the stent 400, thereby forming side holes 410 having cross sections such as those illustrated in FIGS. 4(b) and 4(c). An end mill 500 may also be used to mill side holes 110, 410 with cross-sections as illustrated in FIGS. 1, 4(d) and 4(e) if the end mill 500 is used to cut into the stent wall 102, 402 at a second oblique angle relative to the longitudinal axis of the stent 100, 400 in addition to the first, where the first oblique angle is an acute angle and the second oblique angle is an obtuse angle when measured from the same direction along the longitudinal axis of the stent 100, 400. End mills 500 (or milling tools) having other profiles may also be used to mill side holes 110 in these ways.

Figure 5:
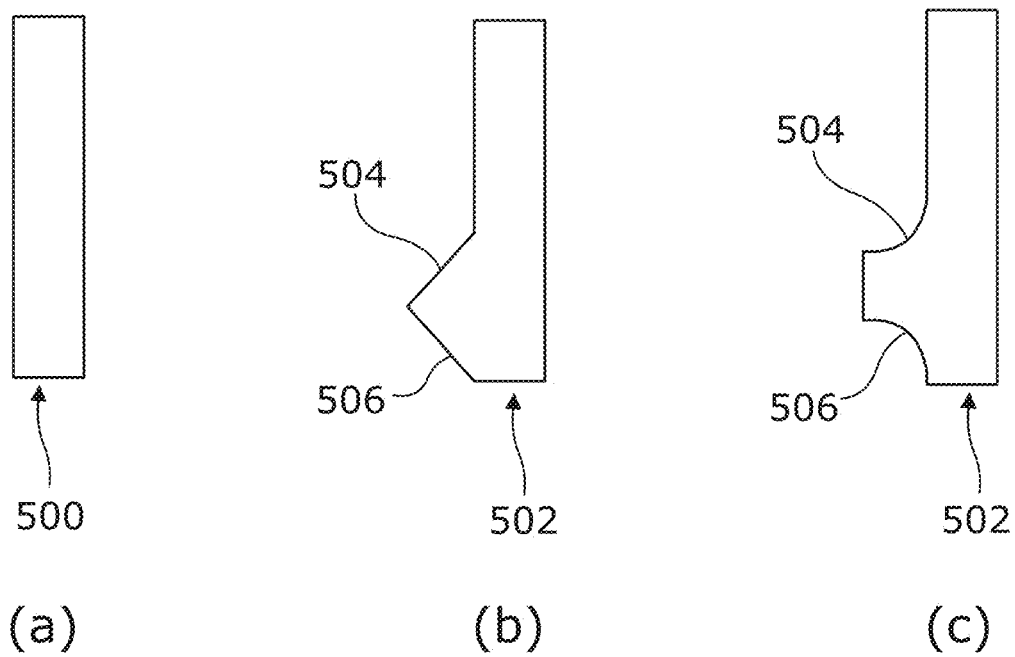
FIG. 5 illustrates various milling tools suitable for use in a method according to the present invention.

Alternatively, specialist milling tools with more complex cutting edges may be employed to cut the side holes 110, 410. For example, the triangular-shaped milling tool 502 illustrated in FIG. 5(b) could be used to form side holes 110, 410 having cross-sections such as those illustrated in FIGS. 1, 4(d) and 4(e). The triangular-shaped milling tool 502 has an upward-facing cutting edge 504 and a downward-facing cutting edge 506, with both the upward- and downward-facing cutting edges 504, 506 being at an oblique angle to the longitudinal axis of the milling tool 502. The downward-facing cutting edge 506 is able to form the portions of the side hole walls 114 that are at an oblique angle to the longitudinal axis of the stent 100 and which face away from the central bore 108 of the stent 100, and the upward-facing cutting edge 504 is able to form the portions of the side hole walls 114 that are at an oblique angle to the longitudinal axis of the stent 100 and which face toward the central bore 108 of the stent 100. The upward- and downward-facing cutting edges 504, 506 of the triangular-shaped milling tool may be straight, as shown in FIG. 5(b), or they may be concave, as shown in FIG. 5(c), which allows the cutting of convex side hole walls, such as those illustrated in FIG. 4(a).

Figure 6:
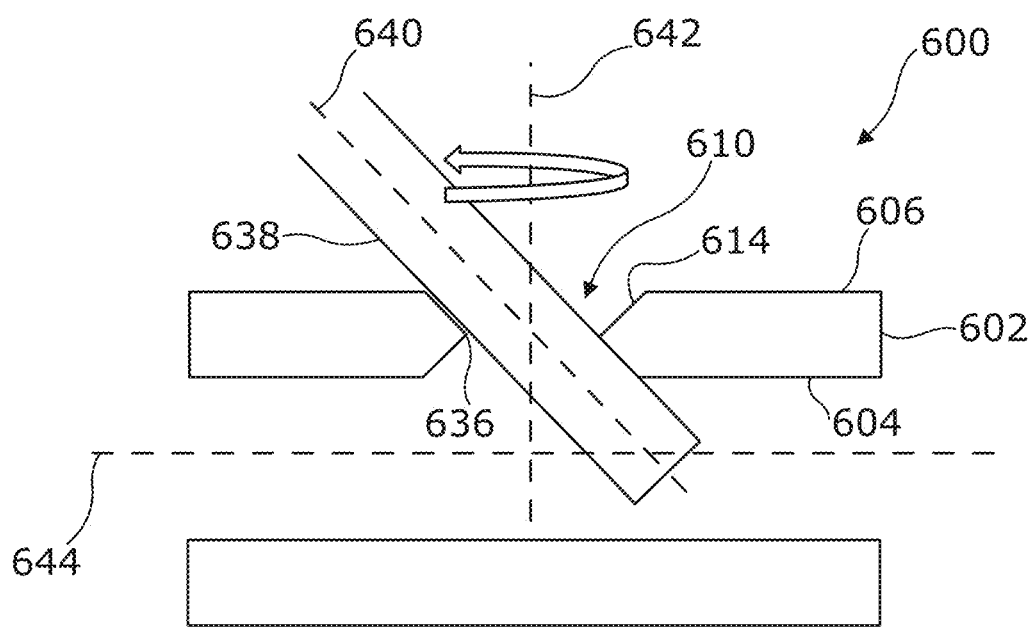
FIG. 6 illustrates a cross-section taken along the longitudinal axis of a portion of a stent according to the present invention showing a side hole being milled using a milling tool.

Referring now to FIG. 6, the side holes 610 may be formed by inserting the milling tool 638 into or through the wall 602 of the stent so that the milling tool 638 (in particular the longitudinal axis 640 of the milling tool 638) is arranged at an oblique angle to the longitudinal (or central) axis 642 of the side hole 610 that is being milled (i.e. the longitudinal axis 642 of the completed or resulting side hole 610) and moving the milling tool 638 and/or the stent 600 to cause the milling tool 638 to rotate (or precess) about the longitudinal axis 642 of the side hole 610 being milled, in particular so that the longitudinal axis 640 of the milling tool 638 rotates or precesses about the longitudinal axis 642 of the resulting side hole 610. This may be achieved either by moving or rotating (e.g. precessing) the milling tool 638 or the stent 600, or a combination of both. For example, the longitudinal axis 640 of the milling tool 638 may remain stationary, while the stent 600 is moved or rotated to effect the relative movement of the stent 600 and the milling tool 638 that is required. For example, the stent 600 or a portion of the stent 600 may be rotated about an axis substantially perpendicular to its longitudinal axis 644. In particular, the stent 600 (or a portion of the stent 600 within which the side hole 610 is being milled) may be rotated in a plane arranged at an oblique angle to the longitudinal axis 640 of the milling tool 638, which provides the required relative rotation or precession of the longitudinal axis 640 of the milling tool 638 about the longitudinal axis 642 of the side hole 610 that is being milled. This process may result in a side hole 610 having a waist or vertex 636 located between the inner 604 and outer 606 surfaces of the stent 600.

The longitudinal axis 642 of the side hole 610 being milled (i.e. the resulting side hole) is generally substantially perpendicular to the longitudinal axis 644 of the stent 600 (or the portion of the stent 600 in which the side hole 610 is formed). Therefore, references to the longitudinal (or central) axis 642 of the side hole should be understood to be interchangeable with references to a rotational axis 642 that may be substantially perpendicular to the longitudinal axis 644 of the stent 600.

Figure 7:
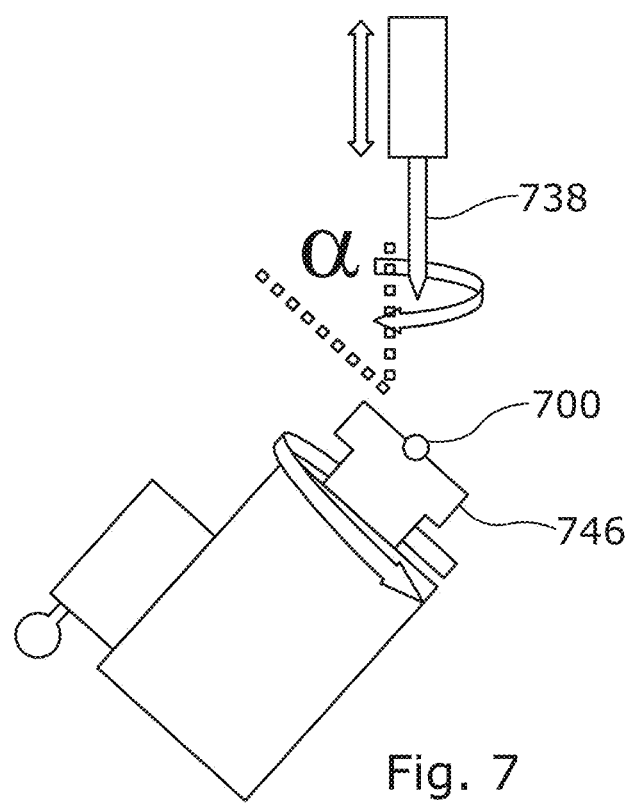
FIG. 7 illustrates a schematic of a milling set-up that may be used to form side holes in accordance with the invention.

As shown in FIG. 7, the stent 700 may be held by a stent holder 746 such that the stent 700, or a portion of the stent held by the stent holder 746, may be rotated in a plane that lies at an oblique angle (a) to the milling tool 738, in particular to the longitudinal axis of the milling tool 738. As such, once the milling tool 738 is inserted into the stent wall, the stent 700 (or portion thereof) may be rotated (as indicated by the arrow) in the oblique plane to form a side hole in accordance with the invention (i.e. with tapered side walls).

Referring again to FIG. 6, preferably, the stent 600 and/or the milling tool 638 are moved such that the longitudinal axis 640 of the milling tool 638 rotates or precesses in the same direction or sense as the milling tool 638 rotates about its longitudinal axis 640. For example, the stent 600 may be rotated in a direction counter to the direction in which the milling tool 638 rotates about its longitudinal axis 640. This improves the accuracy of the milling and provides neater and more accurate side holes 610 with a more uniform profile.

The milling tool 638 may be rotated (or may precess) entirely (e.g. by 360° or more) about the longitudinal axis 642 of the side hole 610 being milled without removing the milling tool 638 from the stent 600. For example, the milling tool 638 may be rotated entirely about the longitudinal axis 642 of the side hole 610 in one movement. However, preferably the stent side hole 610 is milled progressively in steps of less than 360°, with the milling tool 638 removed between each step. For example, the milling tool 638 may be inserted into the stent 600 and rotated about the longitudinal axis 642 of the resulting side hole 610 by a first amount, which is less than 360°, for example, about 180° or about 90° and then removed from the stent 600. In this first step, the milling tool 638 may be rotated about the longitudinal axis of the side hole 642 between a first angle and a second angle through a first angular range. During this first rotational movement, the milling tool 638 forms or mills a first portion of the side hole wall 614, for example the first half or quarter. The milling tool 638 may then be reinserted into the stent 600 and rotated about the longitudinal axis 642 of the side hole 610 by a second, or further, amount, for example by another 180° or 90°. In this second, or subsequent, step, the milling tool 638 may be rotated about the longitudinal axis 642 of the side hole 610 between a third angle and a fourth angle through a second angular range, the second angular range preferably being different to the first angular range. For example, the first angular range may be from 0° to 90° and the second angular range may be from 90° to 180° or from 0° to 180°. During this second rotational movement or step, the milling tool 638 forms or mills a second portion of the side hole wall 614, for example the second half or quarter. The milling tool 638 may then again be removed from the stent 600. This process may be repeated until the side hole 610 is fully formed or milled, with all portions of the side wall 614 formed or milled. In this way, the side hole 610 is milled in a stepwise manner with different portions of the side hole wall 614 being initially milled during different steps, the milling tool 638 being removed from the stent 600 between each step. Thus different steps of the stepwise process form different portions of the stent side hole side wall 614.

In each subsequent step, portions of the side hole wall 614 that were formed in previous steps may be re-milled. In other words, in subsequent steps the milling tool 638 may rotate through angles already covered or milled during previous steps and may also cover additional portions or angles not previously milled. For example, a first portion (e.g. quarter or half) of the side hole wall 614 may be milled in the first step and the second step may involve re-milling the first portion and optionally also newly or initially milling a second portion (e.g. the next or adjacent quarter or half) of the side hole wall 614. This improves the quality of the finish by repeatedly milling portions of the side hole wall 614. Preferably all portions of the side hole wall 614 are milled at least twice. This may be achieved by performing a final complete (i.e. at least 360°) rotation or precession of the milling tool 638 about the longitudinal axis 642 of the stent side hole 610 once all portions of the side hole wall 614 have been milled at least once.

Figure 8:
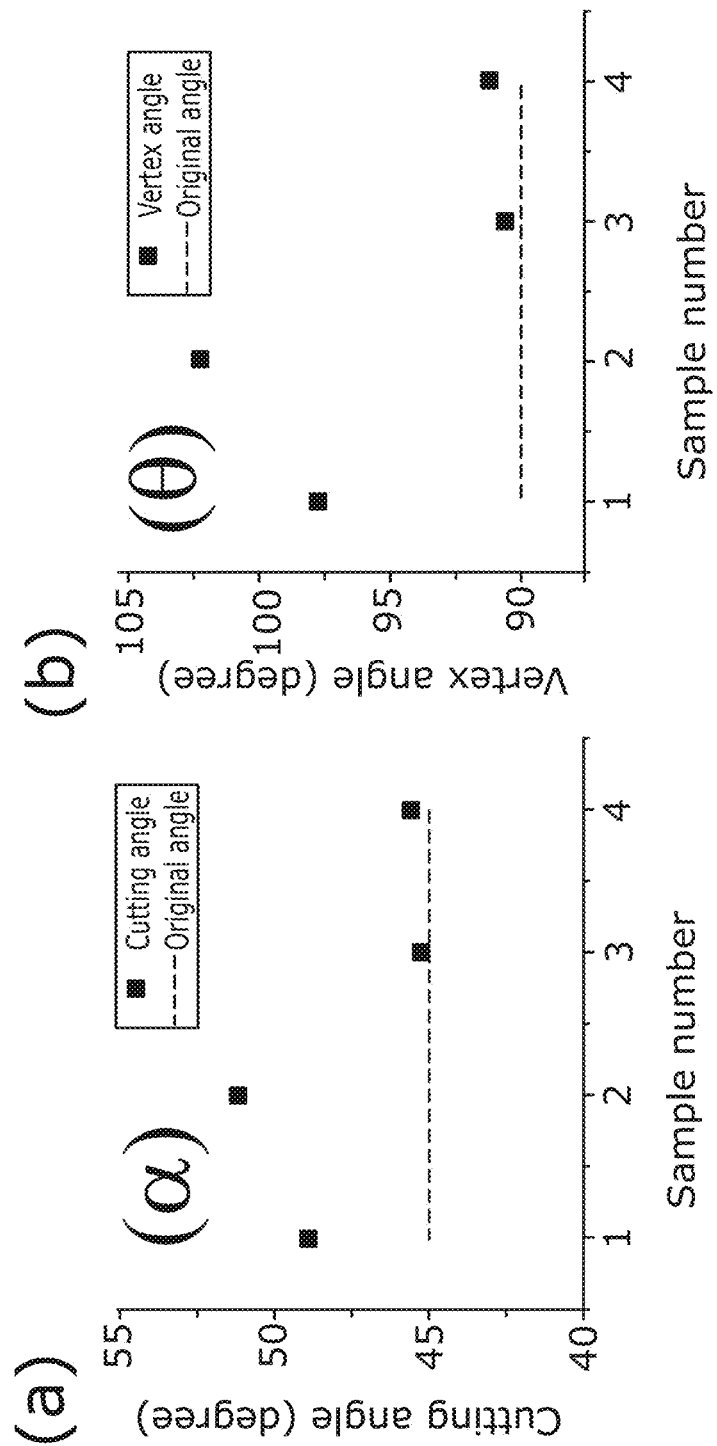
FIG. 8(a) plots the calculated cutting angle for four different side holes (samples 1 to 4). The side holes of samples 1 and 2 were milled using a single rotation of the stent in the oblique plane, whereas samples 3 and 4 were milled using two half rotations and four quarter rotations, respectively, with the milling tool being removed between each step (or rotation). The intended cutting angle was 45°, as indicated by the dashed horizontal line.
FIG. 8(b) plots the calculated vertex angle for four different side holes (samples 1 to 4). The side holes of samples 1 and 2 were milled using a single rotation of the stent in the oblique plane, whereas samples 3 and 4 were milled using two half rotations and four quarter rotations, respectively, with the milling tool being removed between each step (or rotation). The intended vertex angle was 90°, as indicated by the dashed horizontal line.

Surprisingly, the stepwise process described above results in more accurately formed side holes 610 than simply milling the side holes 610 in a single step without removing the milling tool 638 from the stent 600 during the milling process. This is demonstrated by the data presented in FIG. 8. In each of samples 1 to 4 side holes 610 were milled into the side wall of a stent at a cutting angle (a) of 45° to the longitudinal axis 642 of the resulting side hole 610 (i.e. 45° from the rotational axis 642) to form side holes 610 having a waist vertex angle (θ) of 90° located between the inner 604 and outer 606 surfaces of the stent wall 602. The side holes 610 of samples 1 and 2 were milled in a single step (a single round or rotation), whereas the side holes 610 of samples 3 and 4 were milled using two 180° milling steps (two half rounds or rotations) and four 90° milling steps (four quarter rounds or rotations), respectively, removing the milling tool 638 from the stent 600 between steps. Once the side holes 610 were formed, the cutting angle (α) and the vertex angle (θ) were then calculated by measuring various dimensions of the side hole 610, specifically the internal opening diameter, external opening diameter, and waist diameters of the holes. As can be seen from FIGS. 8 (*a*) and (*b*), the measured cutting (α) and vertex angles (θ) for samples 3 and 4 are in very close agreement with the actual (original) cutting angle (α) and the intended (original) vertex angle (θ) (dashed horizontal lines), whereas samples 1 and 2 show significant deviations from the target values, thus demonstrating that the stepwise method produces superior results.

Figure 9:
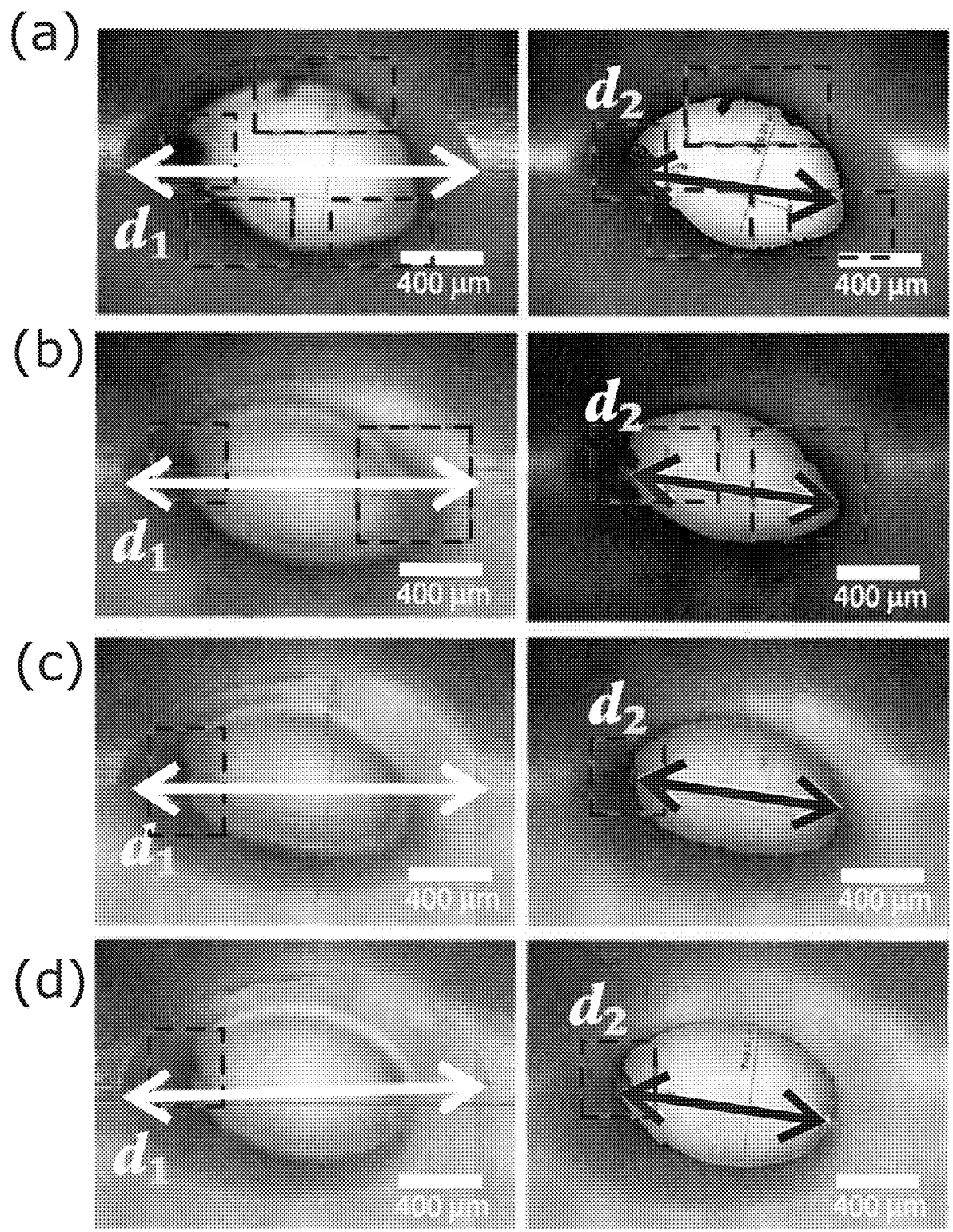
FIGS. 9(a)-(d) show images of side holes focussing on the external surface of the stent (left) and the vertex tip plane (right) for samples 1 (FIG. 9(a)), 2 (FIG. 9(b)), 3 (FIG. 9(c)) and 4 (FIG. 9(d)), as described in relation to FIGS. 8(a) and (b).

FIG. 9 also demonstrates the superior quality of finish provided by the stepwise process. The side holes of samples 1 and 2 (FIGS. 9 (*a*) and (*b*)) are clearly more misshapen and include an increased number of defects (such as the debris, fractures, and bumps highlighted by the dashed boxes) compared to those of samples 3 and 4 (FIGS. 9 (*c*) and (*d*)).

In general, the side holes 110 may be formed either before or after the central bore 108 of the stent 100 is formed.

Many materials from which stents 100 are fabricated, such as polymers and silicone-based materials are flexible. This makes the accurate milling of side holes 110 difficult to achieve. The milling process may therefore further involve cooling the stent 100 prior to milling, for example to a temperature of −130° C. or less, or −180° C. or less, for example to about −196° C. For example, the stent 100 may be cooled sufficiently to prevent the stent 100 from flexing when milled, which facilitates the accurate milling of side holes 110. For example, the stent 100 may be cooled to ensure that the stent 100 material has a Young's modulus of at least 2 GPa, at least 3 GPa, at least 4 GPa, or at least 5 GPa, for example about 5 GPa, when milled when milled (measured by tensile testing, for example using standard test method ASTM D638, for example at a strain rate of 0.6 mm/min on a 30 kN capacity servohydraulic testing machine under displacement control).

The stent 100 may be continuously cooled during the milling process, or may be milled a sufficiently short time after cooling so as to ensure that the stiffening of the stent 100 due to cooling is sufficient to allow accurate milling of the side holes 110. For example, the stent 100 may be milled within 5 minutes, 2 minutes, 1 minute, 30 seconds, or 10 seconds of the end of the cooling process.

The stent 100 may be cooled using liquid nitrogen. For example, the stent 100 may be cooled by immersion in liquid nitrogen.

Another way of facilitating the accurate milling of side holes 110 in flexible stents 100 is to insert a support into the central lumen or bore 108 of the stent 100 to provide rigidity to the stent 100. The support is inserted into the stent 100 before milling is performed, and is removed once the milling is complete. The support may be in the form of a cylindrical core which provides mechanical support to the stent wall 102 during milling and prevents or reduces deformation of the stent wall 102. The support may be formed from a polymer, such as PVC, or other material suitable for milling.

Alternatively, the stents 100 according to the present invention may be formed by an injection moulding process. The mould used in the injection moulding process may be shaped to form a stent 100 with side holes 110. Stents 100 having side holes 110 other than those of the present invention (i.e. those without tapered side walls 114) may also be formed by the injection moulding process of the present invention. Like milling, injection moulding provides a more accurate method of forming side holes 110 than the conventional method of punching the side holes 110 in the stent wall 102 once the stent 100 is already formed. It is also more time-efficient as a separate punching process is not required.

The injection moulding method may comprise the step of removing the stent 100 from the mould by dissolving the mould in acid. The mould may contain aluminium. For example, the mould may be formed of at least 90%, at least 95%, or at least 99% aluminium, or may be formed entirely from aluminium. The acid may be hydrochloric acid, which will not dissolve the stent 100 if it is formed from silicone or a polymer-based material. Alternatively or additionally, nitric acid may be used.

The mould may be formed by 3D printing. For example, the mould may be 3D printed from a polymer and then subsequently coated in aluminium. Alternatively, the mould may be 3D printed directly from aluminium.

The invention claimed is:

1. A stent comprising a stent wall having an inner surface and an outer surface, wherein the inner surface of the stent wall defines a central bore, and wherein the stent wall has a plurality of side holes extending therethrough, and
    wherein each side hole has an upstream end and a downstream end, and wherein the stent wall tapers in thickness in a direction towards the side hole at the upstream and/or downstream end of at least one of the side holes,
    wherein the stent wall tapers away from both the inner surface and the outer surface of the stent wall at the upstream and downstream ends of the at least one of the side holes; or
    wherein the at least one of the side holes extends through the stent wall at an oblique angle relative to the longitudinal axis of the stent.

2. A stent according to claim 1, wherein the stent wall tapers in thickness to form a vertex located between and offset in the radial direction of the stent from both the inner surface and the outer surface of the stent wall.

3. A stent according to claim 2, wherein the vertex is located half way between the inner surface and outer surface of the stent wall.

4. A stent according to claim 2, wherein the vertex has an internal angle of 30 to 120°.

5. A stent according to claim 1, wherein the stent wall tapers away from the inner surface of the stent wall but does not taper away from the outer surface of the stent wall at the upstream end of the at least one of the side holes.

6. A stent according to claim 1, wherein the stent wall tapers away from the outer surface of the stent wall but does not taper away from the inner surface of the stent wall at the upstream end of the at least one of the side holes.

7. A stent according to claim 1 wherein the stent wall tapers away from the inner surface of the stent wall but does not taper away from the outer surface of the stent wall at the downstream end of at the at least one of the side holes.

8. A stent according to claim 1 wherein the stent wall tapers away from the outer surface of the stent wall but does not taper away from the inner surface of the stent wall at the downstream end of at the at least one of the side holes.

9. A stent according to claim 1, wherein the stent has an upstream plurality of side holes in an upstream portion of the stent and a downstream plurality of side holes in a downstream portion of the stent, wherein the upstream plurality of side holes extend through the stent wall at an acute angle relative to the longitudinal axis of the stent when measured from the upstream direction, and wherein the downstream plurality of side holes extend through the stent wall at an obtuse angle relative to the longitudinal axis of the stent when measured from the upstream direction.

10. A stent according to claim 1, wherein the side holes in which the stent wall tapers in thickness in a direction towards the side hole at the upstream and/or downstream end of the side holes are confined to the upstream end of the stent.

11. A stent according to claim 1, wherein the stent wall tapers linearly.

12. A stent according to claim 1, wherein the stent wall tapers to form a convex or a concave profile.

13. A stent according to claim 1, wherein each of the plurality of side holes has a minimum diameter in the direction of the longitudinal axis of the stent of 0.5 to 3.0 mm.

14. A stent according to claim 1, wherein the stent wall has a thickness of 0.2 to 1.0 mm.

15. A method of making a side hole in a stent wall, wherein the method comprises cutting a side hole in the stent wall by micro-milling, wherein the side hole is milled in a stepwise process using a milling tool, the milling tool being removed from the stent between each step.

16. A method of making a side hole in a stent wall, wherein the method comprises cutting a side hole in the stent wall by micro-milling, wherein: the side hole is milled in a stepwise process using a milling tool, the milling tool being removed from the stent between each step;

one step of the stepwise process forms one portion of the stent side hole and another step of the stepwise process forms a different portion of the side hole;

each step of the stepwise process comprises moving the stent and/or the milling tool to cause relative rotation of the milling tool about the longitudinal axis of the resulting side hole; and the longitudinal axis of the resulting side hole is substantially perpendicular to the longitudinal axis of the portion of the stent in which the side hole is formed.

17. A method according to claim 15, wherein the method further comprises inserting a support into the central bore of the stent to support the stent wall during the milling of the side hole.

18. A method according to claim 15, wherein the method further comprises cooling the stent to a temperature of −130° C. or less prior to milling, wherein the stent is cooled using liquid nitrogen.

19. A stent according to claim 1, wherein the stent is formed by injection moulding.

* * * * *